(12) United States Patent
Kerherve et al.

(10) Patent No.: US 7,465,426 B2
(45) Date of Patent: Dec. 16, 2008

(54) SYSTEM FOR DEGASSING MUDS AND FOR ANALYSING THE GASES CONTAINED IN THE MUDS

(75) Inventors: Joseph Kerherve, San Donato (IT); Nicolas Lhermet, Meylan (FR)

(73) Assignee: Geolog S.p.A., Potenza (IT)

( * ) Notice: Subject to any disclaimer, the term of this patent is extended or adjusted under 35 U.S.C. 154(b) by 947 days.

(21) Appl. No.: 10/846,653

(22) Filed: May 17, 2004

(65) Prior Publication Data
US 2004/0265176 A1 Dec. 30, 2004

(30) Foreign Application Priority Data
Jun. 27, 2003 (FR) .................................. 03 07773

(51) Int. Cl.
G01N 15/06 (2006.01)
G01N 7/00 (2006.01)
B01D 51/08 (2006.01)
E21B 47/10 (2006.01)
E21B 47/00 (2006.01)

(52) U.S. Cl. ............................ 422/68.1; 422/83; 95/29; 95/30; 73/152.18; 73/152.43

(58) Field of Classification Search ................ 422/68.1, 422/83; 95/29, 30; 73/152.18, 152.43
See application file for complete search history.

(56) References Cited

U.S. PATENT DOCUMENTS 2,363,247 A 11/1944 Holder
3,151,958 A 10/1964 Bodine
3,284,991 A 11/1966 Ploeger et al.
3,904,392 A 9/1975 VanIngen et al.
4,319,482 A 3/1982 Bunner
4,887,464 A 12/1989 Tannenbaum et al.
5,090,256 A * 2/1992 Issenmann ............... 73/863.23
5,199,509 A 4/1993 Wright et al.
5,447,052 A 9/1995 Delaune et al.
5,648,603 A 7/1997 Hanson
6,443,001 B1 * 9/2002 Duriez et al. ............. 73/152.19

FOREIGN PATENT DOCUMENTS

EP 0 370 548 A1 5/1990
FR 2 819 424 A1 7/2002

* cited by examiner

Primary Examiner—Water D Griffin
Assistant Examiner—Lessanework T Seifu
(74) Attorney, Agent, or Firm—Oliff & Berridge, PLC

(57) ABSTRACT

A tank is fed with mud via a first inlet and the mud is removed via a first outlet. An ultrasonic electroacoustic transducer generates an acoustic energy field in the mud contained in the tank so as to extract the gases from the mud. A carrier gas is injected via a second inlet of the tank and a physico-chemical analysis apparatus of the extracted gases is connected to a second outlet of the tank designed for the carrier gas and the extracted gases. The flow rate of mud fed to the tank is regulated to a constant value and the volume of mud in the tank is constant. The mud can be constituted by oil prospecting drilling mud, the gases to be extracted then being oil revealing gases. The mud feed and injection of carrier gas can be synchronized so as to enable continuous analysis or batch analysis.

13 Claims, 2 Drawing Sheets

SYSTEM FOR DEGASSING MUDS AND FOR ANALYSING THE GASES CONTAINED IN THE MUDS

BACKGROUND OF THE INVENTION

The invention relates to a system for degassing muds and for analysing the gases contained in the muds, a system comprising:
- a tank comprising a first inlet and a first outlet for the mud,
- feed means of the mud, connected to the first inlet of the tank,
- means for extracting the gases from the mud contained in the tank,
- means for injecting a carrier gas, connected to a second inlet of the tank,
- means for physico-chemical analysis of the extracted gases, connected to a second outlet of the tank, designed for the carrier gas and the extracted gases.

STATE OF THE ART

The invention concerns extraction and analysis of gases present in muds and applies in particular to detection of revealing gases such as hydrocarbon and non hydrocarbon gases present in the drilling muds obtained when oil field prospecting operations are performed. For these prospecting operations, the practice is for drill-holes to be made and for the drilling mud to be pumped to the surface to clear the drill-hole and be analysed. These muds are more or less fluid heterogeneous media with a density of about 1 to 2 kg/l, liable to also contain gases and solid fractions of rocks. These gases can be dissolved in the muds or trapped in the porosities of the solids. The presence, among these gases, of hydrocarbon gases ranging from light compounds containing one, two or three atoms of carbon to heavy compounds containing eight atoms of carbon or more has for a long time been considered as a reliable revealing factor representative of the interest of the drilling-hole from the oil-bearing standpoint. Other non hydrocarbon revealing gases, for example Argon, $H_2S$ and $CO_2$, can provide complementary information of geological nature on the interest of the drilling-hole, but these gases are often more difficult to detect. To be able to detect such gases and measure their quantity per unit of volume of mud with precision, they first have to be extracted from the mud in a precise, reliable and fast manner.

Extraction of the gases trapped in drilling muds can be performed in several different manners.

The document U.S. Pat. No. 4,319,482 describes an extraction method based on a vacuum chamber. However, this method is not suitable for the difficult conditions encountered in the field when drilling operations are performed, as such a system is fragile and does not resist large temperature variations.

The documents U.S. Pat. No. 5,199,509 and U.S. Pat. No. 5,648,603 describe a rotary mechanical stirring technique performed by a propeller with several arms driven by a motor and acting on a tank containing the mud. The drawback of this method is that the propeller stirs the mud in the tank in very inhomogeneous manner. The mud situated on the trajectory of the arms of the propeller is greatly stirred whereas that situated under the axis of the propeller is not. Consequently, this method does not enable extraction yields as high as what is desirable to be obtained, in particular for heavy gases corresponding to certain types of hydrocarbons.

The document U.S. Pat. No. 4,887,464 describes an extraction system based on the combination of aerodynamic and mechanical effects and comprising a Venturi effect ejector and a rotating disk. Such a system presents similar limitations to those indicated above for the method described in the U.S. Pat. Nos. 5,199,509 and 5,648,603.

The document U.S. Pat. No. 5,447,052 describes a method consisting in heating the drilling mud by microwave energy to cause degassing thereof. This method can present a risk of chemical modification of the gases or of inflammation.

These known techniques present the drawback of only extracting a fraction of the light gases contained in the drilling muds and do not enable heavy gases containing six, seven or eight or more carbon atoms to be extracted.

OBJECT OF THE INVENTION

The object of the invention is to overcome these drawbacks and, more particularly, to enable degassing of drilling muds and analysis of the extracted gases in a reliable, precise, quantitative and fast manner, in particular by means of a better extraction of the light gases and even more so of the heavy gases.

According to the invention, this object is achieved by the appended claims and, more particularly, by the fact that the extraction means comprise an ultrasonic electroacoustic transducer and that the feed means for feeding mud to the tank comprise volume and flow rate regulating means enabling a preset constant volume of mud to be guaranteed in the tank and enabling the flow rate to be adjusted to a preset constant value.

BRIEF DESCRIPTION OF THE DRAWINGS

Other advantages and features will become more clearly apparent from the following description of particular embodiments of the invention given as non restrictive examples only and represented in the accompanying drawings, in which.

DESCRIPTION OF PARTICULAR EMBODIMENTS

Figure 1:
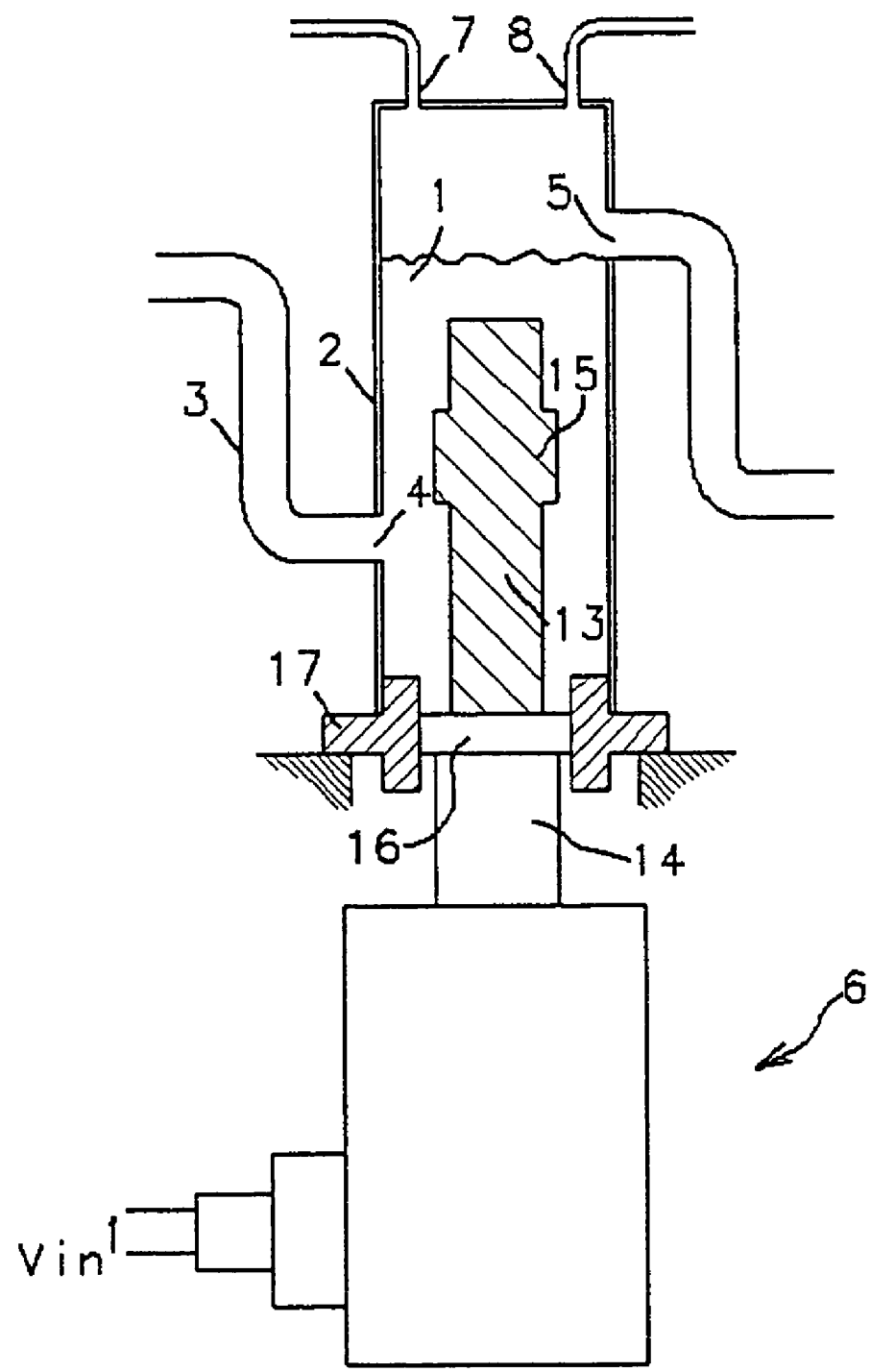
FIG. 1 represents a cross-sectional view of a tank and an electroacoustic transducer of a degassing system according to the invention.

In FIG. 1, mud 1 is input to a tank 2 via a feed pipe 3 connected to a first inlet 4 arranged at the bottom part of a side wall of the tank 2. It is removed via a first outlet 5 arranged at the top part of a side wall of the tank 2 enabling a preset constant volume of mud 1 to be guaranteed in the tank 2 by overflow. The mud thus fills the tank 2 partially in the bottom part up to the level of the first outlet 5. An ultrasonic electroacoustic transducer 6 is designed to generate an acoustic energy field in the mud 1 contained in the tank 2 and thus to extract the gases from the mud. A carrier gas is injected via a second inlet 7 of the tank and removed via a second outlet 8 carrying the extracted gases with it. The second inlet 7 and second outlet 8 are arranged above the first outlet 5 of the mud so that the carrier and extracted gases occupy the top part of the tank 2.

Figure 2:
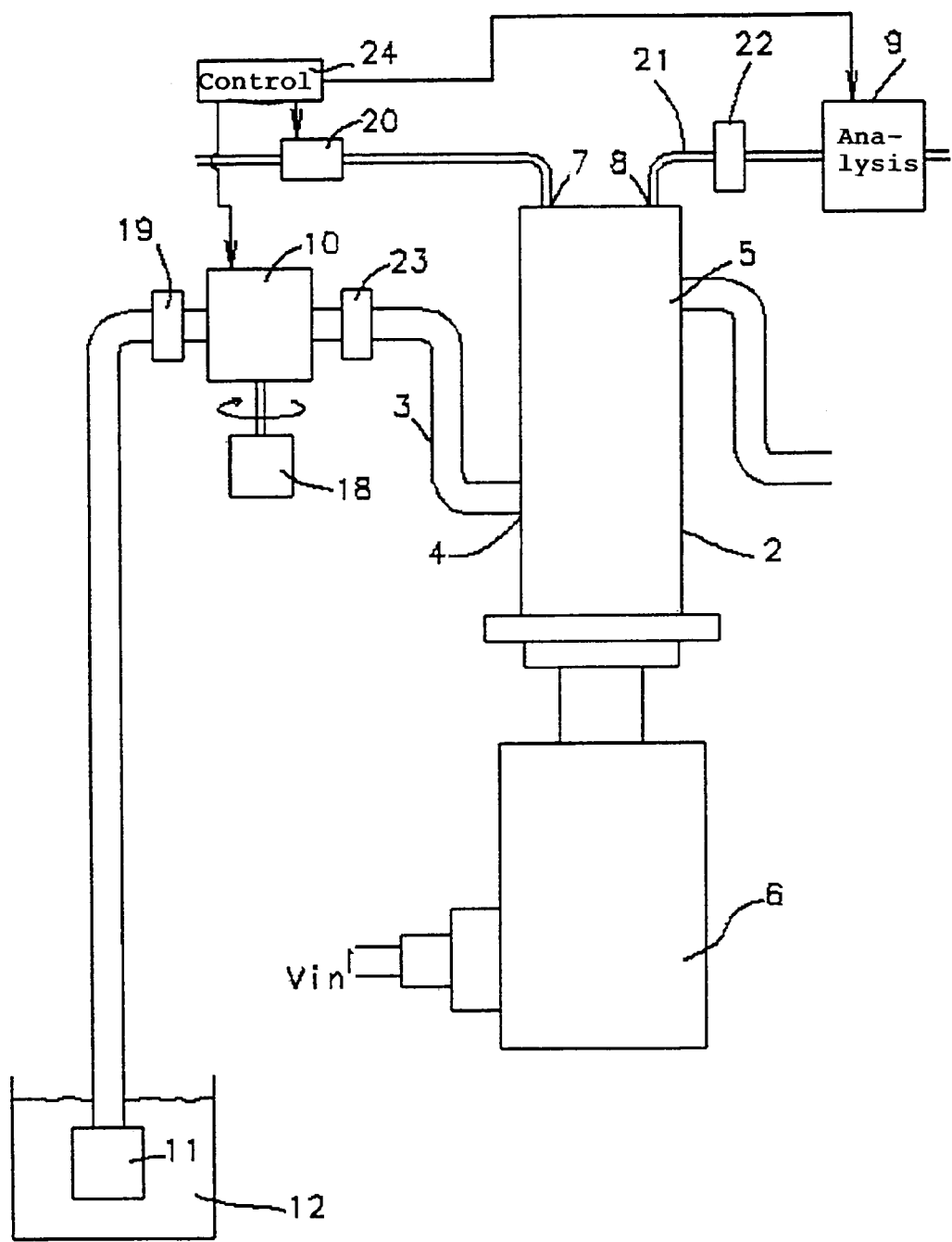
FIG. 2 represents a schematic view of a system for degassing muds and for analysing the gases contained in the muds according to the invention.

As represented in FIG. 2, the second outlet 8 is connected to an apparatus 9 for physico-chemical analysis of the extracted gases. The feed pipe 3 feeding mud to the tank is connected to a pump 10 enabling the flow rate of mud 1 inlet to the tank 2 to be adjusted to a preset constant value. The pump draws the mud, by means of a suction unit 11, from a tank 12, for example a storage tank or a hopper containing for example mud from oil prospecting drilling, the gases to be extracted being in this case oil revealing gases.

Although the document U.S. Pat. No. 3,284,991 disclosed, in 1966, degassing of liquids, in particular of caustic soda, by ultrasounds, the device described is only designed to eliminate the bubbles present in the liquid. It does not in any way enable gases extracted from the liquid to be analysed.

In a system according to the invention, generation of acoustic energy enables up to twice as many light gases and up to four times as many heavy gases to be extracted from oil drilling mud as known systems do. Regulating volume and flow of the mud enables the quantity of gases per unit of volume of mud to be measured with precision and calibrated, quantitative and comparative analysis to be performed by adjusting the flow rate to a constant value comprised, for example, between 1 and 3 l/min, according to the types and conditions of the muds. Thus the sensitivity of analysis can be up to four times higher than that of known systems, for heavy gases. The system enables measurements of gases coming from different muds made at different times to be compared.

The electroacoustic transducer 6 preferably comprises a vibrating part 13 in contact with the mud 1. The electroacoustic transducer 6 is preferably 6 an ultrasonic piezoelectric transducer integrating a piezoelectric converter 14. The converter transforms the input electrical voltage $V_{in}$ into vibrating mechanical energy. The converter 14 can typically be a Langevin type piezoelectric converter operating on resonance, but other types of converters can also be used such as electromagnetic, magnetostrictive or electrostrictive converters. The vibrating part 13 is set into mechanical vibration by the converter 14 and converts these vibrations into an acoustic energy field in the mud 1. The vibrating part 13 is preferably a sonotrode, which in addition enables the mechanical vibrations produced by the converter to be amplified. It can for example be cylindrical and offer a salient part 15. The resonance frequency of the converter 14 is identical to that of the vibrating part 13. The operating frequency of the transducer is close to or greater than 20 kHz, which enables operation to be obtained that is inaudible for human beings. It can even be higher than 40 kHz so as to be inaudible for animals.

The distance between the top end of the part 13 and the filling level of the tank 2 on the one hand, and the distance between the walls of the part 13 and the inside walls of the tank 2 on the other hand, are preferably comprised between a quarter wavelength and four times the wavelength of the ultrasounds in the mud.

The vibrations of the vibrating part 13 are transferred to the mud 1 in the form of acoustic pressure. Preferably, ultrasonic vibrations of strong amplitude are used to produce acoustic fields of strong intensity and to cause the cavitation phenomenon in the mud. The strong pulsing energies of this phenomenon are particularly efficient to extract the gases from the mud and porosities of the solid particles that trap them as they enable these particles to be broken up. The extracted gases join together in bubbles and ascend naturally to the top part of the tank 2.

The transducer 6 preferably comprises an interface 16 with a base 17 of the tank 2 to achieve in particular tightness of the tank 2. The interface 16 is preferably situated at a vibration node of the transducer 6 in order not to disturb or dampen the vibrations of the vibrating part 13. The interface 16 can for example comprise elastomer seals (not shown) to achieve tightness.

As represented in FIGS. 1 and 2, the first inlet 4 and first outlet 5 are preferably placed at opposite points of the tank 2 so that the flow of mud 1 runs along the largest possible surface of the vibrating part 13.

The carrier gas injected via the second inlet 7 is different from the gases sought for in the analysis. In the case of looking for revealing gases in the drilling mud, the carrier gas can quite simply be filtered dry air. In the case where a more precise analysis of the extracted gases is required, the carrier gas can be hydrogen, helium or nitrogen. The carrier gas is non polluted and suited to the analysis apparatus 9 used. The second inlet 7 and second outlet 8 are preferably situated opposite points of the top part of the tank 2, above the level of the mud, so as to carry off a maximum of gas extracted from the mud 1.

With reference to FIG. 2, the pump 10 is preferably a peristaltic pump enabling the flow rate of mud 1 injected into the tank 2 to be mastered with precision. The pump 10 can be driven by a controllable-speed rotary, electric or hydraulic motor 18. This type of motor provides flexibility in so far as it enables the speed of rotation of the pump 10 to be changed easily and the flow rate to be modified, according to the type of mud 1, to adjust it to the constant value required. In order to protect the pump 10 and prevent solid bodies of too large a size from entering the tank 2, a filter 19 can be placed upstream from the pump 10, between the pump 10 and suction unit 11. Nevertheless, the mud injected into the tank may contain particles of millimetric or sub-millimetric size. The filter 19 is preferably self-cleaning, for example by wire brushes driven by a motor. The filter can also be of the linear pneumatic vibrator type, for example at 2000 oscillations per minute, which presents the advantage of being compact, reliable and air-fed, which eliminates the high cost of an electric device in an explosive, and therefore detonatory, environment.

A regulated carrier gas flow rate pump 20 can be placed upstream from the second inlet 7 of the tank 2. The physicochemical gas analysis apparatus 9 is typically a mass spectrometer or a chromatograph, for example of the type using flame ionization detection ("FID"). In the case of a FID chromatograph, the carrier gas used is a flammable gas, whereas the gas is preferably neutral if a mass spectrometer is used.

The distance separating the analysis apparatus 9 from the tank 2 can be about one hundred meters. Over such distances, the carrier gas and extracted gases can cool and possibly condense along ducts 21 connecting the second gas outlet 8 to the analysis apparatus 9, which can decrease the sensitivity and precision of analysis. To prevent cooling of the gases, a heating device 22 of the carrier gas and extracted gases can be fitted downstream from the second outlet 8 of the tank 2. An electric cable can for example be wound around the ducts 21 to heat them by Joule effect.

A heating device 23 of the mud 1, for example an electric induction system, can, if necessary, be fitted upstream from the first inlet 4 of the tank 2, in particular to improve degassing of the cold mud. Muds coming from drilling in deep water can in fact have a temperature of 5° C., substantially lower than the temperature of land drilling muds, which is typically comprised between 50° C. and 70° C. In an alternative embodiment, the tank 2 can be heated by electric induction or by means of electric cables wound around the tank 2 for heating by Joule effect.

A control circuit 24 is designed to perform synchronization of the flows of the mud 1 and gases and of analysis of the gases, by controlling the pump 10, pump 20 and analysis apparatus 9. Synchronization can be adapted to two modes of analysis, continuous or batch. In the case of continuous analysis, the carrier gas flow velocity is preferably equal or close to that of the mud flow.

In another embodiment, not represented, valves placed on the inlet and outlet ducts of the gases and mud 1 perform opening and closing of the mud and gas ducts. It is thus possible to switch from continuous analysis mode to batch analysis mode. The valves are preferably electrovalves electrically controlled by the control circuit 24 in a manner suited to the analysis mode selected.

A batch analysis enables the system to be calibrated, for example, to enable the total quantities of gases contained in the mud to be known, in continuous analysis, without having to effectively perform complete extraction of the gases. For example, the tank is filled making use of the fact that the mud outlet pipe is placed above the mud inlet pipe to enable the excess mud to overflow, then the pump is stopped or the mud inlet valve is closed. From this fixed volume of mud contained in the tank, representing a sample, ultrasonic degassing is engaged to extract the gases to measure the quantity of extracted gases versus time. This makes it possible to determine, after a total extraction time of about ten minutes, the total quantity of gas contained in the sample and, thereby; the fraction of gas extracted after a shorter time than the total extraction time. A comparison of the total quantity of gas extracted with the quantity of gas extracted in continuous operation enables the extracted gas fraction as a function of the flow rate to be determined. For gas extraction from a second sample, the mud inlet valve is opened during a sufficiently long time for the previous mud sample to be completely replaced by new mud, preferably by pumping a quantity of mud several times greater than the volume of the tank, while the ultrasonic transducer 6 is switched off. It is also necessary, for gas extraction from a second sample, for the gas ducts 21 downstream from the second outlet 8 of the tank 2 to be empty of residues of gases extracted when extraction of the previous sample was performed. When the system comprises two distinct gas lines downstream from the tank, it is then possible to switch from one line to the other. The mud inlet valve is then closed and the ultrasonic transducer 6 is switched on for gas extraction from the second sample.

Calibration enables the ratios between the quantities of gases extracted per litre of mud for a given degassing time and the total quantities of gases contained to be known. When switching back to continuous processing, this calibration result is directly applicable knowing the mud flow rate, to know the total quantities of gases contained without having to extract them fully. This process allows higher flow rates than without calibration and can result in time saving.

The invention is not limited to the embodiments represented. In particular, the transducer 6 can be arranged at the top part of the tank 2. It can also be fixed onto the bottom of the tank 2 which vibrates and plays the role of vibrating part 13 in contact with the mud 1.

In an alternative embodiment, the pump 10 feeding the tank 2 with mud 1 can be associated to a pressure regulator and to a servo-controlled proportional valve (not shown). Servo control can be performed by means of a flow rate sensor or a valve opening position sensor.

Moreover, the degassing system according to the invention can be used for analysing any muds. In sludge produced by sewage treatment plants, the system according to the invention enables the quantity and nature of the bio-gases contained in the sludge to be detected efficiently and thus enables the energy potential of these sludges to be checked to recover the bio-gases, should their recovery prove of interest.

The invention claim is:

1. A system for degassing muds and for analysing the gases contained in the muds, the system comprising:
   a tank comprising a first inlet and a first outlet for the mud;
   feed means of the mud, connected to the first inlet of the tank;
   means for extracting the gases from the mud contained in the tank;
   means for injecting a carrier gas, connected to a second inlet of the tank;
   means for physico-chemical analysis of the extracted gases, connected to a second outlet of the tank, designed for the carrier gas and the extracted gases;
   synchronization means of flow rate regulating means;
   carrier gas injection means; and
   physico-chemical analaysis means,
   wherein the extraction means comprise an ultrasonic electroacoustic transducer, and the feed means for feeding mud to the tank comprise volume and the flow rate regulating means enabling a preset constant volume of mud to be guaranteed in the tank and enabling the flow rate to be adjusted to a preset constant value.

2. The system according to claim 1, wherein the muds are oil drilling muds able to contain solid particles of millimetric size, and the gases to be extracted are oil revealing gases.

3. The system according to claim 1, wherein the ultrasonic electroacoustic transducer is a piezoelectric transducer.

4. The system according to claim 3, wherein the transducer comprises a sonotrode arranged, at least partially, inside the tank.

5. The system according to claim 4, wherein the first inlet and first outlet of the mud are arranged so that the mud passes along the sonotrode.

6. The system according to claim 1, wherein the regulating means comprise a peristaltic pump.

7. The system according to claim 6, wherein the regulating means comprise a suction unit and filtering means, upstream from the peristaltic pump.

8. The system according to claim 1, comprising a regulated gas pump, upstream from the carrier gas inlet.

9. The system according to claim 1, comprising heating means for heating the mud.

10. The system according to claim 9, wherein the heating means for heating the mud are arranged upstream from the first inlet of the tank.

11. The system according to claim 1, comprising heating means for heating the carrier gas and the extracted gases, downstream from the second outlet of the tank.

12. The system according to claim 1, comprising synchronization means of the regulating means, carrier gas injection means and physico-chemical analysis means, enabling continuous analysis.

13. The system according to claim 1, comprising control means of the regulating means, carrier gas injection means and physico-chemical analysis means, enabling batch analysis.

* * * * *